United States Patent [19]

Towlerton et al.

[11] 4,192,886

[45] Mar. 11, 1980

[54] METHODS FOR TREATING GASTROINTESTINAL DISEASE

[75] Inventors: Richard G. Towlerton, Burton Joyce, England; Michel Lapras, Ecully, France

[73] Assignee: Fisons Limited, London, England

[21] Appl. No.: 907,558

[22] Filed: May 19, 1978

[30] Foreign Application Priority Data

Jun. 1, 1977 [GB] United Kingdom .............. 23067/77
Aug. 12, 1977 [GB] United Kingdom .............. 33847/77

[51] Int. Cl.² .................... A61K 31/52; A61K 31/42; A61K 31/35
[52] U.S. Cl. .................................. 424/283; 424/253; 424/272
[58] Field of Search .................... 424/283, 253, 272

[56] References Cited

PUBLICATIONS

The Merck Veterinary Manual, third edition, (1967), pp. 6 & 1610.

*Primary Examiner*—Sam Rosen
*Attorney, Agent, or Firm*—Merriam, Marshall & Bicknell

[57] ABSTRACT

There is described a method for the prophylactic or curative treatment of a disease condition of the gastrointestinal tract, which condition has an allergic basis, in cattle or pigs, which comprises administering an active ingredient having sodium cromoglycate like activity to an animal suffering, or liable to suffer, from such a condition.

There are also described compositions and mixtures for use in the treatment of the animals.

17 Claims, No Drawings

METHODS FOR TREATING GASTROINTESTINAL DISEASE

This invention relates to a novel method of treatment of animals, and to novel compositions.

According to the invention we provide a method for the prophylactic or curative treatment of a disease condition of the gastrointestinal tract, which condition has an allergic basis, in cattle or pigs, which comprises administering an active ingredient having sodium cromoglycate like activity to cattle or a pig suffering, or liable to suffer, from such a condition.

A compound having sodium cromoglycate like activity is able to inhibit the release of pharmacological mediators which result from the in vivo combination of certain types of anti-body and specific antigen, for example the combination of reaginic antibody and specific antigen (see Example 27 of British patent specification No. 1,292,601—the rat passive cutaneous anaphylaxis test).

The active ingredients may be characterised by the following biological tests and results thereof.

The compound is first tested in the rat passive cutaneous anaphylaxis test. If the compound does not show significant inhibition of allergic manifestations at 20 mg/kg intraperitoneally (i.p.) or intravenously (i.v.) in this test, its activity is generally too low. Various other biological tests may be used to show that the compound exhibits its anti-allergy activity as an inhibitor of mediators of anaphylaxis rather than as, for example an end organ antagonist or anti-cholinergic and adenyl cyclase stimulator. Therefore, tests to see if the compound inhibits the effect of histamine, serotonin, and slow reacting substance of anaphylaxis (SRSA), that is, that the compound is an end organ antagonist of the mediators, may be employed. Such tests are well known and include contraction of guinea pig ileum in the presence of methysergide for serotonin activity. If activity is still observed in these systems, it is due to histamine action. A further check on histamine is through the spectrofluorimetric assay described by Shore, Burkhalter and Cohn, Journal of Pharmacology and Experimental Therapeutics, Vol 127 page 182. Active ingredients according to the invention are not end organ antagonists.

If the results from these tests show that the active ingredient is not an end organ antagonist further tests may be run to show that the compound is not exhibiting its activity through anti-cholinergicity, e.g. by the reversal of acetylcholine induced guinea pig tracheal chain contraction. An active ingredient will not be an anti-cholinergic.

Specific groups of active ingredients are to be found among the chromone-2-carboxylic acids, and suitable derivatives thereof, e.g. those described in British Patent Specifications Nos. 1,368,243; 1,144,905; 1,230,087 and West German Patent Specification No. 2,553,688. Other active ingredients are to be found among the xanthones, e.g. of Belgian Patent Nos. 759,292 and 787,843 and Dutch Patent Specification Nos. 72,09622 and 73,06958; among the compounds of Belgian Patent No. 792,867; among the azapurines, e.g. of Belgian Patent No. 776,683; the oxazoles, e.g. of West German No. OLS 2,459,380; and the flavones, e.g. of Belgian Pat. No. 823,875.

Particularly preferred are the chromones and chromone like compounds of British patent specifications Nos. 1,144,905; and 1,230,087 and West German Patent Specification No. 2,553,688. More specifically we prefer compounds of formula I,

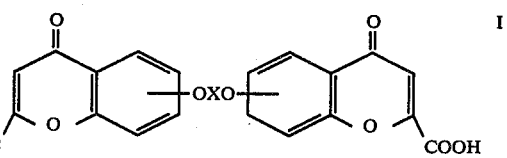

wherein X is a polymethylene chain containing 3 to 7 carbon atoms inclusive, which chain may be substituted by an —OH group, or a pharmaceutically acceptable derivative thereof.

We particularly prefer 1,3-bis(2-carboxychromon-5-yloxy)propan-2-ol or a pharmaceutically acceptable derivative, e.g. salt such as the disodium salt, thereof; this latter is commonly known as sodium cromoglycate or cromolyn sodium. As further preferred compounds there may be mentioned 6,7,8,9-tetrahydro-4-oxo-10-propyl-4H-naphtho[2,3-b]pyran-2-carboxylic acid and 6,7,8,9-tetrahydro-5-hydroxy-4-oxo-10-propyl-4H-naphtho[2,3-b]pyran-2-carboxylic acid and pharmaceutically acceptable derivatives of either thereof. Suitable pharmaceutically acceptable derivatives include salts, alkyl C 1 to 10 esters, mono-alkyl C 1 to 10 amides, di-alkyl C 1 to 10 amides or an unsubstituted amide of the 2-carboxylic acid groups.

Specific conditions to be treated by the method of the invention include those in which allergy or immune reactions play a contributory part.

Gastrointestinal disturbances and enteritis in young pigs and cattle can result in neo-natal diarrhoea and fluid loss often leading to death. Such conditions may be treated by the method of the invention (especially oral administration of active ingredient) as may also diarrhoeas of somewhat older animals which may occur during, or shortly after, the period of liquid feeding. Such diarrhoeas have an infective and/or viral (e.g. Rotavirus and Coronavirus) and/or hypersensitive aetiology, e.g. caused by soya bean meal, or by endotoxins produced by certain pathogenic serotypes of *E. coli*, or by viruses associated with transmissible gastroenteritis.

The active ingredient may be administered by any convenient route which will produce adequate blood levels of the active ingredient or which will treat the organ causing the condition, e.g. the gut, directly. Thus the active ingredient may be administered intravenously, intramuscularly, subcutaneously or preferably orally, The active ingredient to be administered by the method of the invention may if desired be admixed with one or more other compound which are tolerated by the animal by the chosen method of administration. Thus for oral administration the active ingredient may be admixed with inert diluents, such as talc, dextran, lactose, calcium phosphate, water etc. The active ingredient may also be admixed with the animal's foodstuff, e.g. milk, or with other matter which it is desired to administer to the animal orally. Thus the active ingredient may be admixed with desirable trace elements such as copper, cobalt, manganese or a mixture thereof; with one or more vitamins, e.g. vitamins A, D, $B_1$, $B_2$, $B_6$, $B_{12}$, E (or other anti-oxidants) or a mixture thereof; antibiotics (to assist in the prevention of a neonatal scour), for example broad spectrum antibiotics such as chlortetracycline hydrochloride, oxytetracyclin and nitrofurans; absorption aids, e.g. certain amino acids and/or electrolytes; immunoglobulins; or corticosteroids.

Particular compositions for oral administration which may be mentioned are fluid compositions, e.g. a drench, which may be administered with a drenching gun or bottle or a similar device adapted to administer a metered dose to the animal. The drench may be supplied in the form of a wettable powder which can then be dispersed or dissolved in water by the user. Such a powder may compromise the active ingredient, a colloid to make the drench of suitable viscosity for the gun, and a surface active agent to assist dispersion or dissolution of the powder in water. The drench may also be supplied in liquid form in which case it is desirable to incorporate a preservative, e.g. chloroform, glycerin or sodium benzoate. The active ingredient may also be presented in the following forms:

as a tablet containing active ingredient, binder, moistening agent, disintegrant and lubricant; or as a capsule containing active ingredient, binder, moistening agent and lubricant; or as a pill or bolus containing active ingredient and syrup or treacle; or as a paste containing active ingredient, gum and preservative; or as an aerosol pack containing active ingredient, surface active agent, propellant and optionally water.

The aerosol, drench and paste compositions may also, if desired, contain a suitable flavouring to help prevent rejection of the composition by the animal. The compositions should of course be in such a form that the required dose may be administered easily, e.g. as a single unit dose, to the animal. Preferred compositions from the point of view of ease and certainty of oral administration are those which are solids or pastes.

The active ingredient may be administered orally to the animal in conventional manner, for example tablets, capsules, pills and boluses may be placed at, or shot or flicked into the back of the animals mouth and pastes may be smeared carefully on tongue, teeth and the inside of the animals mouth. The active ingredient may also be administered by other techniques, for example liquids and pastes may be administered from a bottle or gun adapted to eject a metered dose, and aerosol compositions may also be put up in containers adapted to eject a metered dose. Such bottles, guns and containers containing a composition comprising the active ingredient form a further feature of our invention.

The oral treatment of gastrointestinal disturbances is most appropriately carried out on young calves and pigs, e.g. during the first 12 weeks, and preferably during the first 21 days, of the animal's life. The calves to be treated for gastrointestinal disturbances are preferably in the weight range 40-60 kg and may be of the type suitable for rearing in intensive fattening units. Such calves are usually male.

The dosage of active ingredient to be administered will of course vary with the active ingredient, the condition to be treated, with its location and severity, with the method of administration and the size of the animal. However we have found that in general the active ingredient may be administered intravenously, intramuscularly or subcutaneously at a daily dosage of up to about 15 mg/kg, e.g. from about 5 to 15 mg/kg, and preferably about 10 mg/kg of animal body weight. When i.v. administration is used the administration preferably takes at least 60 seconds.

We prefer to administer the active ingredient orally. Thus we prefer to administer a daily dosage of up to 1500, preferably from 10 to 500 and more preferably 10 to 200 mg of active ingredient to piglets, and from about 50 to 1000 mg, preferably 50 to 500 mg and more preferably about 100 mg of active ingredient to calves.

The dosages mentioned above may be administered as split doses from 1 to 4 times, and preferably once or twice, a day.

The method of the invention enhances the weight gain of the animal as compared to untreated animals.

The invention is illustrated, but in no way limited by the following Examples.

EXAMPLE 1

A diarrhoea epidemic effecting 50% of the calves and causing a 10% mortality, despite antibiotic treatment, was experienced in an organisation raising calves for slaughter.

10 of the calves were treated from birth for 21 days with disodium cromoglycate at a daily dose of 100 mg (administered as a single daily dose dissolved in 100 ml of milk).

None of these calves contracted diarrhoea and no cases of death were noted amongst them.

EXAMPLE 2

A litter of 6 pigs of 3 weeks of age were used. These animals had suffered from diarrhoea since birth and had been treated on two occasions with antibiotics. Each treatment was of 3 days duration and resulted in cessation of diarrhoea for one or two days.

3 pigs were treated with disodium cromoglycate at the rate of 25 mg daily for 3 days, the compound being administered as a single daily dose dissolved in 5 ml of water.

The diarrhoea ceased in the treated pigs after two treatments and did not recur during the period of observation i.e. 1 week.

We claim:

1. A method for curative treatment of a disease condition of the gastrointestinal tract, which condition has an infective, viral, or hypersensitive aetiology, in cattle or pigs, which comprises administering an active ingredient having sodium cromoglycate like activity to cattle or a pig suffering, from such a condition.

2. A method according to claim 1 wherein the active ingredient is a compound of formula I, $$\text{HOOC} \underset{O}{\overset{O}{\bigcirc}} \text{—OXO—} \underset{O}{\overset{O}{\bigcirc}} \text{COOH} \quad I$$

wherein X is a polymethylene chain containing 3 to 7 carbon atoms inclusive, which chain may be substituted by an —OH group, or a pharmaceutically acceptable salt thereof.

3. A method according to claim 1, wherein the active ingredient is sodium cromoglycate.

4. A method according to claim 1, wherein the animal is a neo-nate.

5. A method according to claim 1, wherein the condition is diarrhoea.

6. A method according to claim 1, wherein the active ingredient is administered directly to the gut.

7. A method according to claim 1, wherein the active ingredient is administered intravenously, intramuscularly or subcutaneously.

8. A method according to any one of the preceding claims, wherein the active ingredient is administered in admixture with one or more other compounds which are tolerated by the animal by the chosen method of administration.

9. A method according to claim 8, wherein the active ingredient is administered orally in admixture with talc, dextran, lactose, calcium phosphate, water, the animal's foodstuff, copper, cobalt, manganese or a mixture thereof; one or more vitamins; an antibiotic; an absorption aid; an imunoglobulin; or a corticosteroid.

10. A method according to claim 1, wherein the active ingredient is administered in the form of a drench, tablet, capsule, pill, bolus, paste or aerosol.

11. A method according to claim 1, wherein a gastrointestinal disturbance is treated in a calf or pig during the first 12 weeks of its life.

12. A method according to claim 11, wherein the treatment is carried out during the first 21 days of the animal's life.

13. A method according to claim 1, wherein the active ingredient is administered intravenously, intramuscularly or subcutaneously at a dosage of 5 to 15 mg per kg of animal body weight.

14. A method according to claim 1, wherein a daily dosage of 10 to 1500 mg of active ingredient is administered to a piglet orally.

15. A method according to claim 14, wherein the daily dosage is 10 to 500 mg.

16. A method according to claim 15, wherein the daily dosage is from 10 to 200 mg.

17. A method according to claim 1, wherein a daily dosage of from 50 to 1000 mg of active ingredient is administered to a calf.

* * * * *